United States Patent

Weyer et al.

Patent Number: 5,536,854
Date of Patent: Jul. 16, 1996

[54] PREPARATION OF 2-METHYL-1,4-BUTANEDIOL AND 3-METHYLTETRAHYDROFURAN

[75] Inventors: Hans-Juergen Weyer, Mannheim; Rolf Fischer, Heidelberg; Franz Merger, Frankenthal; Juergen Frank, Limburgerhof; Jochem Henkelmann, Mannheim; Hardo Siegel, Speyer; Thomas Ruehl, Frankenthal, all of Germany

[73] Assignee: BASF Aktiengesellschaft, Ludwigshafen, Germany

[21] Appl. No.: 380,134

[22] Filed: Jan. 26, 1995

Related U.S. Application Data

[63] Continuation of Ser. No. 124,027, Sep. 21, 1993, abandoned.

[51] Int. Cl.$^6$ .............. C07D 307/06; C07D 307/08; C07C 29/141; C07C 29/149
[52] U.S. Cl. .............. 549/508; 568/862; 568/864
[58] Field of Search ............. 549/508; 568/862, 568/864

[56] References Cited

U.S. PATENT DOCUMENTS

| | | | |
|---|---|---|---|
| 4,124,600 | 11/1978 | Jenkins, Jr. | 260/346.11 |
| 4,940,805 | 7/1990 | Fischer et al. | 549/326 |
| 4,973,717 | 11/1990 | Williams | 549/508 |

FOREIGN PATENT DOCUMENTS

| | | |
|---|---|---|
| 276012 | 7/1988 | European Pat. Off. . |
| WO86/03189 | 6/1986 | WIPO . |
| WO88/00937 | 2/1988 | WIPO . |

*Primary Examiner*—Ba Kim Trinh
*Attorney, Agent, or Firm*—Keil & Weinkauf

[57] ABSTRACT

2-Methyl-1,4-butanediol and 3-methyltetrahydrofuran are prepared by reacting a compound of the general formula I or II

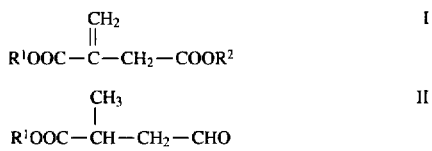

where $R^1$ and $R^2$ are each hydrogen or $C_1$-$C_8$-alkyl and the formyl group of II may also be present as acetal with a $C_1$-$C_8$-alkanol, is reacted with hydrogen in the presence of copper or of a metal of groups 7 to 10 of the Periodical Table of elements or of a compound of these metals.

3 Claims, No Drawings

PREPARATION OF 2-METHYL-1,4-BUTANEDIOL AND 3-METHYLTETRAHYDROFURAN

This application is a continuation of application Ser. No. 08/124,027, filed on Sep. 21, 1993, now abandoned.

The present invention relates to a novel process for the preparation of 2-methyl-1,4-butanediol and 3-methyltetrahydrofuran (3-methyl-THF).

These products have been obtainable to date by different processes.

According to EP-A-277 562, the hydrogenation of citric acid over Pd or Re on $TiO_2$, $ZrO_2$ or carbon leads to 3-methyl-THF and 3- and 4-methylbutyrolactone. However, the selectivity of 70% of 3-methyl-THF is unsatisfactory if it is intended to carry out the process on a large industrial scale.

U.S. Pat. No. 3,956,318 describes the conversion of alkyl-substituted ω-hydroxyepoxides to 3-methyl-THF with hydrogen at from 50° to 250° C. and from 0.7 to 350 bar over catalysts which contain a metal from groups 8 to 10 of the Periodic Table of elements. According to U.S. Pat. No. 3,975,449, 2-methyl-1,4-butanediol can be prepared from these starting compounds at from 20° to 200° C. under otherwise identical conditions. Neither of the two processes is attractive since the preparation of the starting compounds is expensive.

JP-A 49/9463, JP-A 49/9464 and JP-A 50/1038 describe the preparation of, inter alia, methyl-γ-butyrolactone and/or 3-methyl-THF by hydrogenation of methylmaleic or methylfumaric acid. In these cases, too, the preparation of the starting materials is expensive. The processes furthermore involve technically complicated measures (temperature control or a certain arrangement of the catalyst).

According to U.S. Pat. No. 3,859,369, the hydroformylation of but-2-ene-1,4-diol, isolation of the catalyst and hydrogenation of the reaction mixture lead to 2-methyl-1,4-butanediol, which can be converted into 3-methyl-THF by acidic catalysis. However, the hydroformylation of the internal double bond is possible only with a low yield, the main product always being 1,4-butanediol. Chiral 2-methyl-1,4-butanediol can be prepared from the chiral diester of 2-methylsuccinic acid by catalytic hydrogenation (DE-A 3 801 863).

It is an object of the present invention provide a process for the preparation of 2-methyl-1,4-butanediol and 3-methyl-THF which does not have the stated disadvantages.

We have found that this object is achieved by a process for the preparation of 2-methyl-1,4-butanediol and 3-methyl-THF, wherein a compound of the formula I or II

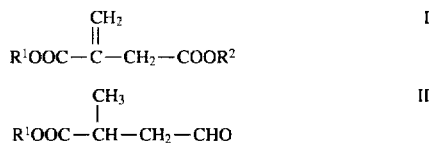

where $R^1$ and $R^2$ are each hydrogen or $C_1$-$C_8$-alkyl and the formyl group of II may also be present as acetal with a $C_1$-$C_8$-alcohol, is reacted with hydrogen in the presence of copper or of a metal of groups 7 to 10 of the Periodical Table of elements or of a compound of these metals.

The starting compounds I are iraconic acid ($R^1$ and $R^2$ are each hydrogen) or $C_1$-$C_8$-alkyl monoesters or diesters thereof. The alkyl groups are, for example, methyl, ethyl, n-propyl, isopropyl, n-butyl and isobutyl. However, iraconic acid itself is preferred and can be very advantageously prepared by fermentative sugar degradation (eg. U.S. Pat No. 3,044.941).

The starting compounds II are derived from 3-formyl-2-methylpropionic acid. The alkyl radicals are radicals such as ethyl, n-propyl, n-butyl and isobutyl, but preferably methyl. Ethyl 3-formyl-2-methylpropionate can be prepared in good yield and selectivity by hydroformylation of methyl methacrylate (Bull. Chem. Soc. Japan 50 (1977), 2351). The aldehyde function may also be present in the form of an acetal with a $C_1$-$C_8$-alkanol.

The catalysts contain, as essential components, copper or a metal of groups 7 to 10 of the Periodic Table of elements. Among these last-mentioned metals, rhenium, cobalt, nickel, ruthenium, rhodium, palladium and platinum are preferred. Catalysts which contain copper are preferred. Since the catalysts are, as a rule, activated with hydrogen, the active components are predominantly in metallic form.

The catalysts may contain further components. These are, for example, zinc, chromium, molybdenum, tungsten and manganese, as well as acidic compounds, such as mineral acids, eg. sulfuric acid, phosphoric acid and hydrochloric acid, Lewis acids, such as boron trifluoride and zinc chloride, and heteropoly acids, such as tungstophosphoric acid.

The catalysts can be used in compact form, ie. without a carrier, but preferably as supported catalysts. The type of carrier material is as a rule not critical. Conventional carrier materials, such as silica, alumina, titanium dioxide, zirconium dioxide, active carbon, silicates and zeolites, may therefore be used.

If necessary, binders or molding assistants may be used for the preparation of the catalysts.

The catalysts are prepared by conventional methods, for example by precipitating carbonates and hydroxides of the active metals and of the carrier compounds together, molding the product, calcining the moldings and activating them with hydrogen.

The supported catalysts may have any form, for example chips, spheres, cylinders, strands or rings.

The reaction can be carried out in the presence or absence of a solvent. Examples of suitable solvents are ethers, such as tetrahydrofuran, alcohols, in particular $C_1$-$C_8$-alkyl alcohols, such as methanol, ethanol and isopropanol, and water, as well as mixtures of these solvents.

The reaction temperatures are preferably from 100° to 350° C., particularly preferably from 150° to 250° C. The pressure may be chosen within wide limits of from 1 to 400 bar but is preferably from 50 to 300 bar. The reaction can be carried out in the gas or liquid phase, batchwise or continuously. In the case of fixed-bed catalysts, the liquid-phase or trickle-bed procedure can be chosen. It is also possible to use suspended catalysts.

Catalyst space velocities of from 0.01 to 1, preferably from 0.05 to 0.3, kg of starting material per kilogram of catalyst per hour have proven useful.

The reactors used may be, for example, stirred kettles, tube reactors or tube-bundle reactors.

The reaction mixture obtained can be separated in a known manner, preferably by distillation.

The novel process permits the simple preparation of 2-methyl-1,4-butanediol and 3-methyl-THF from readily available starting materials.

It has been found that a high reaction temperature, a low catalyst space velocity and the use of catalysts which contain an acidic component generally lead to formation of a higher proportion of 3-methyl-THF.

2-Methyl-1,4-butanediol is a useful component for the synthesis of polyethers or polyesters. 3-Methyl-THF serves as a comonomer for the preparation of polytetrahydrofurans, which are further processed to resilient fibers (EP-A 343 985).

EXAMPLES

The catalysts used in the Examples have the following composition (data in % by weight): Catalyst A 67% of CoO
19.8% of CuO
7% of $Mn_2O_3$
3% of $MoO_3$
0.2% of NaO
3% of $H_3PO_4$
(according to EP-B 100 406, page 2, line 63—page 3, line 11)

B 33% of CuO
38% of $Cr_2O_3$
9% of BaO
20% of $H_2O$
(according to DE-A 3 624 812, page 4, lines 35-41; Examples)

C 36.5% of CuO
1% of BaO
0.6% of $Cr_2O_3$
0.4% of ZnO
14.4% of MgO
28.5% of $SiO_2$
18.6% of $H_2O$
(according to DE-A 1 442 981, page 2, 2nd paragraph—page 3)

D 70% of CuO
25% of ZnO
5% of $\gamma$-$Al_2O_3$
(according to DE-A 1 542 632, page 2–page 4, line 2)

E 40% of CuO
20% of ZnO
40% of $\gamma$-$Al_2O_3$
(according to DE-A 1 542 632, page 2—page 4, line 2)

F 40% of CuO
40% of ZnO
19.9% of $\gamma$-$Al_2O_3$
0.1% of $Na_2O$
(according to DE-A 1 542 632, page 2–page 4, line 2)

G 56% of CuO
44% of $Al_2O_3$
(according to EP-A 44 444, page 8, line 33—page 11, line 1)

H 35% of CuO
65% of $\gamma$-$Al_2O_3$
(according to EP-A 44 444, page 8, line 33— page 11, line 1)

I 1% of Ru
1.2% of Sn
1.3% of B
96.5% of $\gamma$-$Al_2O_3$
(according to Ind. Eng. Chem. Res. 28 (1989), 1110)

EXAMPLES 1–9

Methyl 3-formyl-2-methylpropionate in the form of a 20% strength by weight solution in ethanol and 100 l (measured under standard conditions of temperature and pressure) of hydrogen per hour were reacted at 200 bar by the descending procedure over 30 ml of catalyst in the form of from 2.5 to 4 mm chips in a tube reactor (length 20 cm, diameter 16 mm).

The liquid mixture discharged from the reaction was investigated by gas chromatography.

Further details are given in Table 1 below.

TABLE 1

| Example | Catalyst | Catalyst space velocity [kg/kg · h] | Temperature [°C.] | Conversion [%] | Yield [%]*, based on the conversion | |
|---|---|---|---|---|---|---|
| | | | | | Diol | 3-MTHF |
| 1 | A | 0.12 | 225 | 95 | 66 | 6 |
| 2 | B | 0.15 | 250 | 99 | 2 | 90 |
| 3 | C | 0.10 | 250 | 100 | 0 | 85 |
| 4 | D | 0.16 | 250 | 99 | 85 | 4 |
| 5 | E | 0.15 | 250 | 99 | 35 | 53 |
| 6 | F | 0.15 | 250 | 100 | 1 | 91 |
| 7 (without ethanol) | G | 0.15 | 250 | 99 | 1 | 90 |
| 8** | H | — | 250 | 99 | 0 | 82 |
| 9** | I | — | 250 | 100 | 1 | 69 |

Diol = 2-Methyl-1,4-butanediol
3-MTHF = 3-Methyl-THF
*The reaction mixture also contained mainly 3-methyl-$\gamma$-butyrolactone and unidentified compounds.
**Batchwise reaction of 100 g of methyl 3-formyl-2-methylpropionate for 12 hours at a hydrogen pressure of 260 bar over 10 g of catalyst.

EXAMPLES 10–12

Itaconic acid in the form of a 20% strength by weight solution in ethanol and 100 l (measured under standard conditions of temperature and pressure) of hydrogen per hour were reacted at 200 bar and at a temperature T over a catalyst in the form of 2.5–4 mm chips in a tube reactor (length 20 cm, diameter 16 mm). The liquid mixture discharged from the reaction was investigated by gas chromatography.

Further details are shown in Table 2.

TABLE 2

| Example | Catalyst | Amount of catalyst [g] | Catalyst space velocity [kg/kg · h] | Temperature [°C.] | Conversion [%] | Yield [%]*, based on the conversion | |
|---|---|---|---|---|---|---|---|
| | | | | | | Diol | 3-MTHF |
| 10 | A | 29 | 0.10 | 225 | 95 | 66 | 6 |
| 11 | F | 23 | 0.10 | 250 | 97 | 1 | 90 |
| 12 | G | 19 | 0.20 | 250 | 100 | 1 | 91 |

Diol = 2-Methyl-1,4-butanediol
3-MTHF = 3-Methyl-THF
*cf. Table 1

We claim:

1. A process for the preparation of 2-methyl-1,4-butanediol and 3-methyltetrahydrofuran, wherein a compound of the formula II

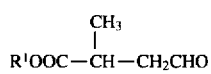

$$R^1OOC-\overset{\overset{\displaystyle CH_3}{|}}{CH}-CH_2CHO \qquad II$$

where $R^1$ is hydrogen or $C_1$-$C_8$-alkyl and the formyl group of II may also be present as acetal with a $C_1$-$C_8$-alkanol, is reacted with hydrogen in the presence of supported or unsupported catalysts consisting essentially of copper and optionally a member selected from the group consisting of zinc, chromium, molybdenum, tungsten, manganese, mineral acids, Lewis acids, and heteropoly acids.

2. A process as defined in claim 1, wherein the starting compound is methyl 3-formyl-2-methylpropionate.

3. A process as defined in claim 1, wherein CuO is used as a catalyst.

* * * * *